United States Patent [19]

Bout et al.

[11] Patent Number: 5,304,291
[45] Date of Patent: Apr. 19, 1994

[54] METHOD OF PREPARING 9BETA, 10ALPHA-5,7-DIENE STEROIDS

[75] Inventors: Berthus Bout; Ronald Voorhaar, both of Weesp, Netherlands

[73] Assignee: Duphar International Research B.V., Weesp, Netherlands

[21] Appl. No.: 21,902

[22] Filed: Feb. 24, 1993

[30] Foreign Application Priority Data

Feb. 27, 1992 [EP] European Pat. Off. ........ 92200564.0

[51] Int. Cl.$^5$ .............................................. C07G 13/00
[52] U.S. Cl. .............................. 204/157.6; 204/157.9; 204/157.91
[58] Field of Search .............. 204/157.6, 157.9, 157.91

[56] References Cited

U.S. PATENT DOCUMENTS 3,219,565 11/1965 Rappoldt .............................. 204/162
4,601,855 7/1986 Rappoldt et al. ........... 260/239.55 C
4,837,481 6/1989 Verstegen et al. ............ 252/301.4 R

OTHER PUBLICATIONS

Dauben et al., J. Am. Chem. Soc., 1982, 104, 355–356 "Wavelength-Controlled Production of Previtamin $D_3$".
Dauben et al, J. Am. Chem. Soc., 1982, 104, 5780–5781 "Effects of Wavelength on the Photochemistry of Provitamin $D_3$".
Malatesta et al, J. Am. Chem. Soc., 1981, 103, 6781–6783 "Laser Photochemical Production of Vitamin D".
Rappoldt et al, 80 (1961) Recueil, 43–46 "Investigations of Sterols XIX" 6-Dehydro-9$\beta$,10$\alpha$-progesterone.
Rappoldt et al, 90 (1971) Recueil, 27–32 "Investigations on Sterols XXXVII" New routes to 9,10-isomers.

*Primary Examiner*—John Niebling
*Assistant Examiner*—Cybille Delacroix-Muirheid
*Attorney, Agent, or Firm*—Stevens, Davis, Miller & Mosher

[57] ABSTRACT

The invention relates to a method of preparing a 9beta,10alpha-5,7-diene steroid by irradiating the corresponding 9alpha,10beta-5,7-diene steroid with filtered ultraviolet light from an indium lamp.

10 Claims, No Drawings

METHOD OF PREPARING 9BETA, 10ALPHA-5,7-DIENE STEROIDS

The invention relates to a method of preparing a 9beta,10alpha-5,7-diene steroid by irradiating the corresponding 9alpha,10beta-5,7-diene steroid or seco-steroid with filtered ultraviolet light.

9Beta,10alpha-5,7-diene steroids generally are intermediates in the synthesis of pharmacologically interesting compounds which can perform a useful function in the human body. The hormone analogue 6-dehydro-9beta,10alpha-progesterone (9beta,10alpha-pregna-4,6-diene-3,20-dione) or dydrogesterone is an orally active progestative hormone and is generally used to correct deficiencies of progesterone in the body.

Therefore, a good possibility for synthesizing this substance and other 9beta,10alpha-steroids from available or readily accessible raw materials is of great importance. Various 9alpha,10beta-steroids, for example, ergosterol, pregnenolone and progesterone, are available as raw materials for the preparation of 9beta,10alpha-5,7-diene steroids. The preparation of dydrogesterone from pregnenolone is described by Rappoldt et al. in Recueil trav. chim. 1961, 80, 43, and 1971, 90, 27. Important intermediates in the synthesis of dydrogesterone are lumisterol$_2$, 3-(ethylenedioxy)-9beta,10alpha-pregna-5,7-diene-20-one and 3,20-bis(ethylenedioxy)-9beta,10alpha-pregna-5,7-diene. These intermediates can be prepared by irradiating the corresponding 9alpha,10beta isomers, namely ergosterol, 9alpha,10beta-3-(ethylenedioxy)-pregna-5,7-diene-20-one and 9alpha,10beta-3,20-bis(ethylenedioxy)-pregna-5,7-diene, respectively, with ultraviolet light. This irradiation is preferably carried out with filtered ultraviolet light. A medium-pressure or high-pressure mercury lamp has so far been used for this purpose. In the above-mentioned publications, the desired 9beta,10alpha-5,7-diene steroids were formed during this photochemical isomerisation in yields of only 20% calculated on converted 9alpha,10beta-isomer. When the UV-irradiation was carried out in two steps, namely first by means of short-wave UV-radiation and then by means of long-wave UV-radiation as described in NL 112,521, the desired 9beta,10alpha-5,7-diene steroid could also be isolated in a yield of not yet 20% calculated on converted starting material. Obviously, a considerable part of the expensive starting material is lost in this photochemical isomerisation, probably due to the formation of undesired side products. It therefore stands to reason that an improvement of the yield in this photochemical conversion is of great importance.

Dauben and Phillips (J. Am. Chem. Soc. 1982, 104, 355 and 5780) state that the desired formation of 9beta,10alpha-5,7-diene steroids can be improved by the application of laser photolysis. The results of Dauben and Phillips, however, are not in conformity with those of Malatesta et al.: J. Am. Chem. Soc. 1981, 103, 6781. Apart from these questionable results, for a practical industrial production the use of lasers is not very attractive in view of the high costs of acquisition and the high energy consumption. Irradiation with a lamp is therefore to be preferred by far to laser irradiation for producing a certain photochemical conversion.

It was found by Rappoldt and Mos (EP 0,152,138), that the photochemical conversion of 9alpha,10beta-5,7-diene steroids or suitable seco-steroids (seco-steroids) into the corresponding 9beta,10alpha-5,7-diene steroids could be performed with a considerably higher yield if an antimony lamp was used as the light source instead of a conventional medium-pressure mercury lamp. If desired, the irradiation can be carried out by using two different lamps in succession, first a conventional light source producing UV-radiation, e.g. a medium-pressure mercury lamp, and then an antimony lamp, to produce comparable results as with an one-lamp irradiation. In this manner 9beta,10alpha-3,20-bis(ethylenedioxy)-pregna-5,7-diene could be prepared by conversion of the corresponding 9alpha,10beta compound in a yield of approx. 30%, calculated on starting material, or of approx. 75%, calculated on converted material, in a reaction time of 6 to 7 hours (Examples I and VII of EP 0,152,138).

The above known process, however, is still unsatisfactory in some respects. First, the production capacity, i.e. the conversion per time unit (per hour), does not fully come up to the producer's expectations. The intrinsic capacity of irradiation processes is always relatively small due to the required dilution of the solution to be irradiated. Therefore, an improved conversion per time unit is very important for effecting a commercially and technically attractive process. Further, an antimony lamp is expensive to operate compared to a medium-pressure mercury lamp.

It is the objective of the invention to considerably improve the capacity of producing 9beta,10alpha-5,7-diene steroids by irradiating the corresponding 9alpha,10beta-5,7-diene steroids or seco-steroids, and, at the same time, to reduce the operating costs.

This objective can be achieved, according to the present invention, by irradiating the above starting 9alpha,10beta-5,7-diene-steroid or seco-steroid with filtered ultraviolet light from an indium lamp. An indium lamp is a medium-pressure or high-pressure mercury lamp endowed with indium. By using this light source in the method of the present invention, the operating techniques and facilities are much easier and simpler than by using an antimony lamp. As will become apparent from the appendant Example, the production capacity, i.e. the desired conversion per time unit, can be improved with a factor of approximately two by using an indium lamp compared to the known antimony lamp as a radiation source.

The above indium lamp can be used according to the method of the invention by passing the steroid-solution through a reservoir surrounding the lamp or by immersing the lamp in the solution to be irradiated. It will be obvious that in the former method of irradiating a number of indium lamps can be used to improve the production capacity, around which lamps the solution to be irradiated can be passed in a continuous flow (annular flow reactor). In the latter method immersion lamps can be used, which are immersed in the solution accommodated in a reaction vessel (immersion photochemical reactor). Such a reaction vessel can be dimensioned in a suitable manner, allowing the use of high-power indium lamps, viz. up to 100 kW.

Preferably the irradiation with the indium lamp is preceded by an irradiation procedure with a conventional light source producing UV-radiation, generally a normal medium-pressure or high-pressure mercury lamp, to achieve optimum results.

In principle, all 9alpha,10beta-5,7-diene steroids or seco-steroids may be used as starting materials for the photochemical conversion of the invention, provided photosensitive substituents in the molecule are preferably protected. For example, it is usually desired to ketalize sensitive ketone functions optionally present in the starting material, before subjecting the material to a photochemical conversion according to the invention. Suitable seco-steroids for the above conversion are previtamin D compounds and tachysterol compounds.

The method according to the invention relates more in particular to the preparation of 9beta,10alpha-5,7-diene steroids from starting steroids or seco-steroids of the general formula

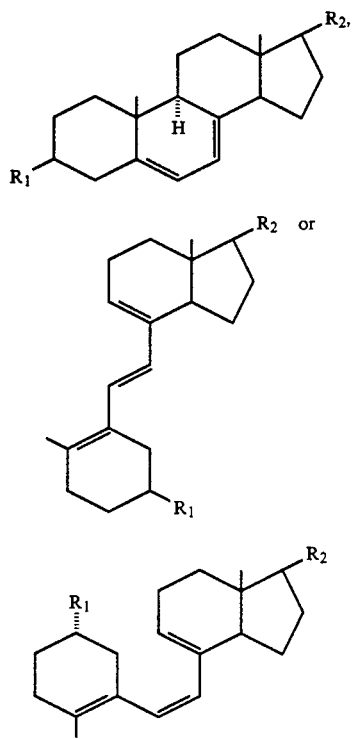

wherein
$R_1$ is a hydrogen atom; an etherified, non-etherified, esterified or non-esterified hydroxy group; or a ketalized or non-ketalized oxo function; and
$R_2$ is a branched or non-branched, saturated or unsaturated aliphatic hydrocarbyl group having 1–16 carbon atoms, which group, if desired, is substituted with one or more substituents selected from fluorine atoms, etherified, non-etherified, esterified or non-esterified hydroxy groups, cyclopropyl groups, and ketalized or non-ketalized oxo functions.

A suitable esterification agent for a hydroxy group in the above molecule is an alkylchlorocarbonate having 2 to 5 carbon atoms, or an aromatic carboxylic acid (e.g. benzoic acid or halo-, nitro- or ($C_1$-$C_4$)alkyl-substituted benzoic acid), a saturated aliphatic carboxylic acid having 1 to 4 carbon atoms, p-toluenesulphonic acid, methanesulphonic acid, trifluoroacetic acid or a derivative of these acids suitable for the esterification reaction (e.g. an acid chloride or acid anhydride).

For etherification of a hydroxy group in principle various etherification agents are suitable: for example, a triphenylmethylhalide, 2,3-dihydropyrane, a trialkylsilylhalide, a diphenylalkylsilylhalide, an alkoxyalkylhalide, a trialkylsilylethoxymethylhalide, or a derivative thereof, the alkyl groups of which have 1 to 6 carbon atoms.

The above term "ketalized" also encompasses thioketalized. For ketalizing purposes various alcohols, thiols, ortho esters or di(thi)ols are suitable, the latter producing cyclic ketals. Example are: methanol, ethanol, ethanethiol, tri(m)ethyl orthoformate, ethylene glycol, propane diol, butane diol and ethylene dithiol.

Examples of suitable starting steroids, which play a part as intermediates in the production of dydrogesterone, are ergosterol, 9alpha,10beta-3,20-bis(ethylenedioxy)-pregna-5,7-diene and 9alpha,10beta-3-(ethylenedioxy)-pregna-5,7-diene-20-one. As will become apparent from the Example, these compounds can conveniently be converted into the desired 9beta,10alpha isomers, namely lumisterol$_2$, 9beta,10alpha-3,20-bis(ethylenedioxy)-pregna-5,7-diene and the corresponding monoketal, respectively, by using the method of the invention. Other suitable starting materials are seco-steroids, in particular previtamins and tachysterols. For example, by using the method according to the present invention, previtamin $D_2$ and 6Z-9,10-seco-3,20-bis(ethylenedioxy)-pregna-5(10),6,8-triene can easily be converted into lumisterol$_2$ and 9beta,10alpha-3,20-bis(ethylenedioxy)-pregna-5,7-diene, respectively; the same products can be prepared by irradiating tachysterol$_2$ and 6E-9,10-seco-3,20-bis(ethylenedioxy)-pregna-5(10),6,8-triene, respectively.

The invention will now be described in greater detail with reference to the following specific example.

EXAMPLE

Preparation of 9beta,10alpha-3,20-bis(ethylenedioxy)-pregna-5,7-diene 40 g of 9alpha,10beta-3,20-bis(ethylenedioxy)-pregna-5,7-diene are dissolved in 4 liters of methyl acetate. The resulting solution is then irradiated with a 1500 W medium pressure mercury lamp (Philips HOV ®), while cooling and in a nitrogen atmosphere. A filter is used which absorbs all the light below a wavelength of 260 nm.

After 1.3 hours a solution is obtained, the dissolved substance of which according to HPLC analysis is composed as follows: 49.5% (19.8 g) of starting material, 33.9% (13.6 g) of 6Z-9,10-seco-3,20-bis(ethylenedioxy)-pregna-5(10),6,8-triene, 3.3% (1.3 g) of 6E-9,10-seco-3,20-bis(ethylenedioxy)-pregna-5(10),6,8-triene and 9.1% (3.6 g) of 9beta,10alpha-3,20-bis(ethylenedioxy)-pregna-5,7-diene. Then the mercury lamp is replaced by an indium lamp (Philips HOV 32/2000 ®) and a filter solution is applied which absorbs all the light below a wavelength of 300 nm.

The solution is irradiated for 2.2 hours and again analysed by HPLC, which gives the following composition of the dissolved substance: 59.9% (24.0 g) of starting material, 4.7% (1.9 g) of 6Z-9,10-seco-3,20-bis(ethylenedioxy)-pregna-5(10),6,8-triene, 0.2% (0.08 g) of 6E-9,10-seco-3,20-bis(ethylenedioxy)-pregna-5(10),6,8triene and 31.0% (12.4 g) of 9beta,10alpha-3,20-bis(ethylenedioxy)-pregna-5,7-triene. Therefore the yield of the desired product, based on consuming starting material, is 77.3%.

We claim:
1. A method of preparing a 9β,10α-5,7-diene steroid comprising irradiating the corresponding 9α,10β-5,7-diene steroid or seco-steroid with filtered ultraviolet light, said irradiation being carried out with an indium lamp.

2. A method as claimed in claim 1, wherein the irradiation is carried out with an indium-doped mercury discharge lamp and, prior to the irradiation with an indium-doped mercury discharge lamp, the starting steroid or seco-steroid is irradiated with a conventional light source, producing UV-radiation.

3. A method as claimed in claim 1, wherein the starting steroid or seco-steroid is a compound of the formula

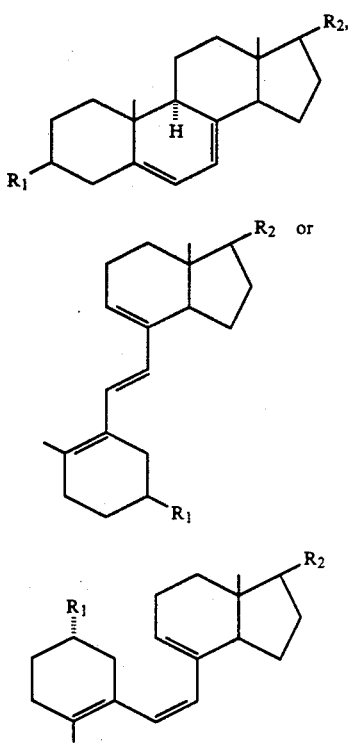

wherein
R₁ is a hydrogen atom; an etherified, non-etherified, esterified or non-esterified hydroxy group; or a ketalized or non-ketalize oxo function; and
R₂ is a branched or non-branched, saturated or non-saturated aliphatic hydrocarbyl group having 1–16 carbon atoms, which group, if desired, is substituted with one or more substituents selected from the group consisting of fluorine atoms, etherified, non-etherified, esterified or non-esterified hydroxy groups, cyclopropyl groups, and ketalized or non-ketalized oxo functions.

4. A method as claimed in claim 3, wherein the starting steroid is selected from the group consisting of ergosterol, 9α,10β-3,20-bis(ethylenedioxy)-pregna-5,7-diene and 9α,10β-3-(ethylenedioxy)-pregna-5,7-diene-20-one.

5. A method as claimed in claim 3, wherein the starting seco-steroid is selected form the group consisting of previtamin D₃ and 6Z-9,10-seco-3,20-bis(ethylenedioxy)-pregna-5(10),6,8-triene.

6. A method as claimed in claim 3, wherein the starting seco-steroid is selected from the group consisting of tachysterol₃ and 6E-9,10-seco-3,20-bis(ethylenedioxy)-pregna-5(10),6,8-triene.

7. A method as claimed in claim 2, wherein the starting steroid or seco-steroid is a compound of the formula

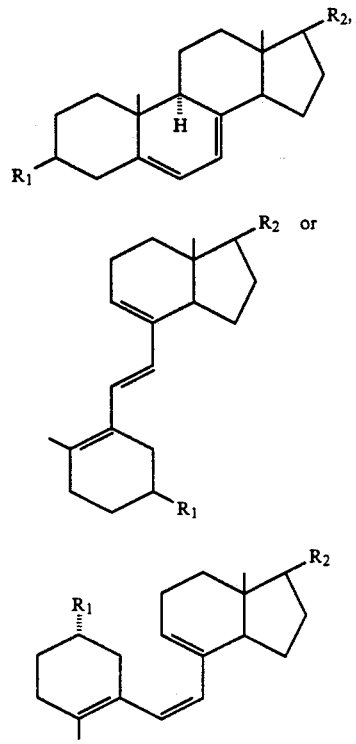

wherein
R₁ is a hydrogen atom; an etherified, non-etherified, esterified or non-esterified hydroxy group; or a ketalized or non-ketalized oxo function; and
R₂ is a branched or non-branched, saturated or non-saturated aliphatic hydrocarbyl group having 1–16 carbon atoms, which group, if desired, is substituted with one or more substituents selected from the group consisting of fluorine atoms, etherified, non-etherified, esterified or non-esterified hydroxy groups, cyclopropyl groups, and ketalized or non-ketalized oxo functions.

8. A method as claimed in claim 7, wherein the starting steroid is selected from the group consisting of ergosterol, 9α,10β-3,20-bis(ethylenedioxy)-pregna-5,7-diene and 9α,10β-3-ethylenedioxy)-pregna-5,7-diene-20-one.

9. A method as claimed in claim 7, wherein the starting seco-steroid is selected from the group consisting of previtamin D₃ and 6Z-9,10-seco-3,20-bis(ethylenedioxy)-pregna-5(10),6,8-triene.

10. A method as claimed in claim 7, wherein the starting seco-steroid is selected from the group consisting of tachysterol₃ and 6E-9,10-seco-3,20-bis(ethylenedioxy)-pregna-5(10),6,8-triene.

* * * * *